(12) United States Patent
Anderson

(10) Patent No.: US 8,025,908 B2
(45) Date of Patent: Sep. 27, 2011

(54) TOPICAL HAIR CARE FORMULATION AND METHOD OF MAKING

(76) Inventor: Lavonda D. Anderson, Richmond, VA (US)

( * ) Notice: Subject to any disclaimer, the term of this patent is extended or adjusted under 35 U.S.C. 154(b) by 113 days.

(21) Appl. No.: 12/578,410

(22) Filed: Oct. 13, 2009

(65) Prior Publication Data

US 2010/0092582 A1 Apr. 15, 2010

Related U.S. Application Data

(60) Provisional application No. 61/105,536, filed on Oct. 15, 2008.

(51) Int. Cl.
*A61K 36/00* (2006.01)
*A61K 36/63* (2006.01)
*A61K 36/53* (2006.01)

(52) U.S. Cl. ................................ 424/725; 424/727
(58) Field of Classification Search .................. None
See application file for complete search history.

*Primary Examiner* — Qiuwen Mi
(74) *Attorney, Agent, or Firm* — Ariel S. Bentolila; Bay Area IP Group, LLC

(57) ABSTRACT

A topical hair care formulation and method of making includes combining generally equal amounts of *eclipta alba* herbal powder and *embelica officinalis* herbal powder to form a herbal powder mixture. The herbal powder mixture is steeped in an amount of base oil for a period of time to form a brown solution. A portion of an amount of olive oil is combined with an amount of biotin and an amount of Methylsulfonylmethane to form a natural mixture. A remainder of the amount of olive oil is combined with the brown solution. An amount of jojoba oil is combined with the brown solution. An amount of rosemary oil is combined with the brown solution. An amount of lavender oil is combined with the brown solution. The natural mixture is combined with the brown solution. The brown solution is settled for a period of time to form the topical hair care formulation.

20 Claims, 1 Drawing Sheet

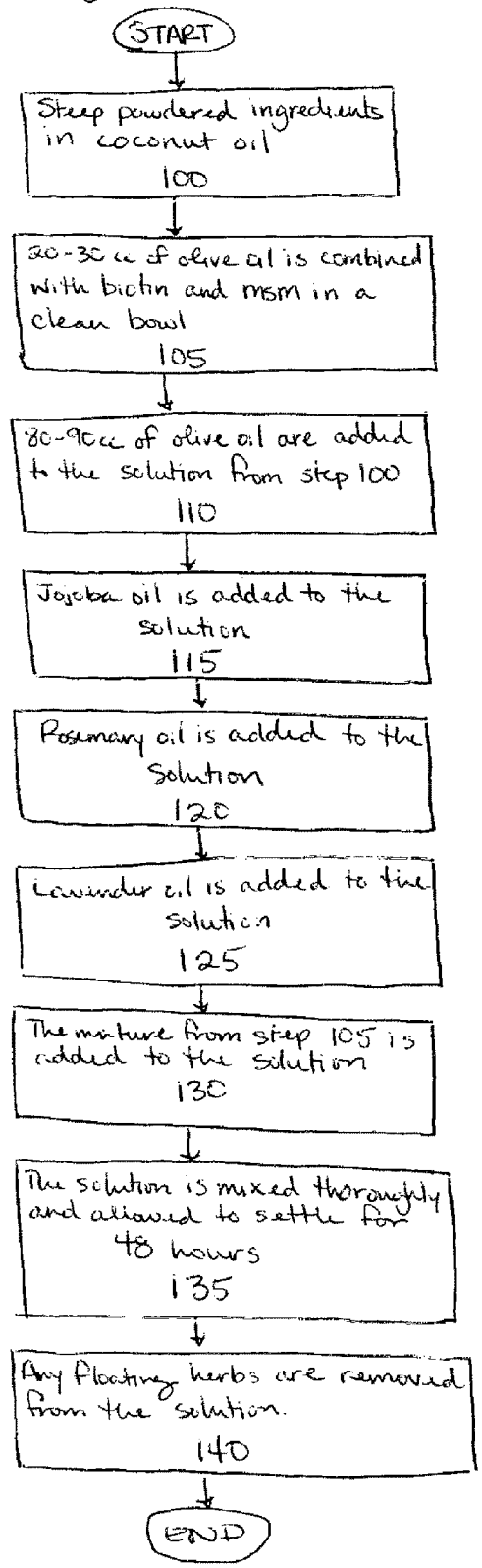

TOPICAL HAIR CARE FORMULATION AND METHOD OF MAKING

CROSS-REFERENCE TO RELATED APPLICATIONS

The present Utility patent application claims priority benefit of the U.S. provisional application for patent Ser. No. 61/105,536 filed on Oct. 15, 2008 under 35 U.S.C. 119(e). The contents of this related provisional application are incorporated herein by reference for all purposes.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates generally to hair care products. More particularly, the invention relates to hair oil for promoting hair health and growth.

BACKGROUND OF THE INVENTION

For years, many men and women have suffered from slow growing hair and hair loss. There are approximately 35 million men and 21 million women in America that are affected by slow growth or hair loss in various degrees. The normal cycles of hair growth can be stunted or altered by several factors including, but not limited to, stress, heredity, and poor diet. Genetics play an important role in the hair growth rate and hair loss and therefore may vary individually. Malnutrition can cause a percentage of hair follicles to stop growing and the remaining follicles to produce fine, fragile hair. Environmental factors, health conditions and medical treatments can have a dramatic effect on hair growth as well. It is therefore an objective of the present invention to provide a solution for quickly growing healthy hair.

In the past, it was believed that there was nothing that could make the hair grow faster or reverse hair loss. Presently, the products on the market that can actually grow hair are expensive, generally require a prescription, and/or take at least one month before results are received. Other known methods for preventing hair loss or growing hair involve surgery, which puts the consumer at risk for the possibility of complications. Sufferers of hair loss, more importantly, have been seeking a fast but safe and effective way to combat slow growth and hair loss for many decades.

In view of the foregoing, there is a need for improved techniques for providing a non-prescription, non-surgical product for easily and quickly growing healthy hair that is inexpensive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1 is a flowchart illustrating an exemplary process for making a topical formulation for promoting hair health and growth, in accordance with an embodiment of the present invention.

Unless otherwise indicated illustrations in the figures are not necessarily drawn to scale.

SUMMARY OF THE INVENTION

To achieve the forgoing and other objects and in accordance with the purpose of the invention, a topical hair care formulation and method of making is presented.

In an embodiment a method of making a topical hair care formulation is presented. The method includes steps for combining herbal powders to form a herbal powder mixture, steps for steeping the herbal powder mixture to form a brown solution, steps for combining biotin and Methylsulfonylmethane to form a natural mixture, steps for combining a olive oil with the brown solution, steps for combining jojoba oil with the brown solution, steps for combining rosemary essential oil with the brown solution, steps for combining lavender essential oil with the brown solution, steps for combining the natural mixture with the brown solution and steps for settling the brown solution to form the topical hair care formulation. Another embodiment further includes steps for removing herbal powder mixture from the topical hair care formulation.

In another embodiment a method of making a topical hair care formulation is presented. The method includes the steps of combining generally equal amounts of *eclipta alba* herbal powder and *embelica officinalis* herbal powder to form a herbal powder mixture. The herbal powder mixture is steeped in an amount of base oil for a period of time to form a brown solution. A portion of an amount of olive oil is combined with an amount of biotin and an amount of Methylsulfonylmethane to form a natural mixture. A remainder of the amount of olive oil is combined with the brown solution. An amount of jojoba oil is combined with the brown solution. An amount of rosemary essential oil is combined with the brown solution. An amount of lavender essential oil is combined with the brown solution. The natural mixture is combined with the brown solution. The brown solution containing the olive oil, jojoba oil, rosemary oil, lavender oil and natural mixture is settled for a second period of time to form the topical hair care formulation. Another embodiment further includes the step of removing any floating herbal powder mixture from the topical hair care formulation. In another embodiment the step of steeping further includes placing the herbal powder mixture in a cloth bag. In yet another embodiment the base oil is coconut oil. In still another embodiment the base oil is avocado oil. In another embodiment the olive oil is extra virgin. In yet another embodiment the lavender essential oil is French lavender essential oil.

In another embodiment a topical hair care formulation is presented. The formulation includes an amount of solution from herbal powders steeped in a base oil. The herbal powders are derived from *eclipta alba* and *embelica officinalis* plants. The formulation includes an amount of biotin and an amount of methylsulfonylmethane combined with an amount of olive oil. The formulation further includes an amount of jojoba oil, an amount of rosemary essential oil and an amount of lavender essential oil. In another embodiment the base oil includes coconut oil. In yet another embodiment the base oil includes avocado oil. In still another embodiment the olive oil is extra virgin. In another embodiment the lavender essential oil is French lavender essential oil. In yet another embodiment a ratio of an amount of herbal powder derived from *eclipta alba* plants to an amount of herbal powder derived from *embelica officinalis* plants is in the order of 1 to 1. In still another embodiment a ratio of the amount of base oil to the amount of olive oil is in the order of 2 to 1. In another embodiment a ratio of the amount of base oil to the amount of jojoba oil is in the order of 6.7 to 1. In yet another embodiment a ratio of the amount of base oil to the amount of lavender essential oil is in the order of 209 to 1. In still another embodiment a ratio of the amount of base oil to the amount of rosemary essential oil is in the order of 94 to 1. In another embodiment a ratio of the amount of methylsulfonylmethane to the amount of biotin is in the order of 200 to 1.

Other features, advantages, and object of the present invention will become more apparent and be more readily understood from the following detailed description, which should be read in conjunction with the accompanying drawings.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention will now be described in detail with reference to embodiments thereof as illustrated in the accompanying drawings.

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Preferred embodiments of the present invention provide a hair care formulation that is applied topically to the scalp. Preferred embodiments provide nourishment to the hair follicle, promoting hair health. More particularly, preferred embodiments of the present invention provide a hair care formulation that may reverse hair loss and may increase the rate of hair growth with regular use. This increase of the normal hair growth rate may reverse hair loss. In preferred embodiments the formulation is a topical composition that comprises a proprietary blend of natural herbs and essential oils to provide the basis for quick, healthy hair growth. Preferred embodiments of the present invention are distinguished over prior art in general in that they provide a natural, in extensive, cost effective, easy to use treatment to combat slow growing hair and hair loss to fulfill the desires, needs, expectations or demands of millions of people. Results produced with use of preferred embodiments of this invention have generally indicated that hair growth can be achieved and hair loss may be reversed in as little as five days. Not all hair bulbs can be excited into activity; however, most can be stimulated into performance with preferred embodiments.

FIG. 1 is a flowchart illustrating an exemplary process for making a topical formulation for promoting hair health and growth, in accordance with an embodiment of the present invention. In the present embodiment, the formulation preferably comprises the following ingredients in the indicated amounts, as shown by way of example in Table 1; 230-240 cc of coconut oil, 110-120 cc of extra virgin olive oil, 30-40 cc of jojoba oil, 0.75-1.5 cc of lavender essential oil, 2.0-3.0 cc of rosemary essential oil, 5000 mcg of biotin, 1000 mg of methylsulfonylmethane, 0.5 tsp of *emblica officinalis* herbal powder, and 0.5 tsp of *eclipta alba* herbal powder. Those skilled in the art, in light of the present teachings, will readily recognize that in alternate embodiments some of the ingredients may be substituted with other ingredients or omitted from the formula, or additional ingredients may be included. For example, without limitation, other types of olive oil may be used in place of the extra virgin olive oil, and in some alternate embodiments, various aromatic ingredients may be included to produce different scents. French lavender essential oil is preferred over lavender essential oil for aromatic purposes. Furthermore, the amount of each ingredient may vary in alternate embodiments. An acceptable range of the ingredients is 40-300 cc of coconut oil, 15-180 cc of olive oil, 5-80 cc of jojoba oil, 0.5-3.5 cc of Rosemary oil, 0.25-2 cc of lavender oil, 500 mcg-7500 mcg of biotin, 250 mg to 2500 mg of methylsulfonylmethane, 0.25-2 tsp of emblica officinalis herbal powder, and 0.25-2 tsp of *eclipta alba* herbal powder.

TABLE 1

| | | |
|---|---|---|
| 230-240 | cc | Coconut Oil |
| 110-120 | cc | Extra Virgin Olive Oil |
| 30-40 | cc | Jojoba Oil |
| 0.75-1.5 | cc | Lavender essential Oil |
| 2.0-3.0 | cc | Rosemary essential oil |
| 5000 | mcg | Biotin |
| 1000 | mg | Methylsulfonylmethane |
| 0.5 | tsp | *Emblica Officinalis* herbal powder |
| 0.5 | tsp | *Eclipta alba* herbal powder |

In the present embodiment, the process begins at step 100 where the powdered ingredients of the formulation, the emblica officinalis herbal powder and the eclipta herbal powder, are placed in a sanitized cloth muslin bag and slowly steeped over warm heat in the coconut oil for 30 to 45 minutes or until the oil turns brown. In an alternate embodiment avocado oil is used instead of coconut oil. In a clean bowl, 20 to 30 cc of the olive oil is combined with the biotin and Methylsulfonylmethane and stirred until mixed thoroughly in step 105 to form a natural mixture. In step 110, the remaining 80 to 90 cc of olive oil is added to the brown solution that comprises the powdered ingredients and the coconut oil that was made in step 100. In step 115, the jojoba oil is added to this brown solution followed by the rosemary oil in step 120 and then the lavender oil in step 125. Lastly, the mixture of the small portion of olive oil, biotin, and methylsulfonylmethane made in step 105 is added to the brown solution in step 130. In step 135 the solution is stirred until mixed thoroughly and then allowed to settle for 48 hours to disperse any floating herbs that were not filtered with the use of the muslin cloth in step 100. The mixture may be allowed to settle for a longer period of time. If there are any floating herbs, they are removed from the solution in step 140, and the hair care formulation is ready for use. Those skilled in the art, in light of the present teachings, will readily recognize that some of the steps in this process may be performed in different sequences. For example, without limitation, the olive oil, biotin, methylsulfonylmethane mixture made in step 105 may be made before the powdered ingredients steep in the coconut oil in step 100 or later in the process for example, without limitation, after the essential oils are added to the coconut oil mixture in step 125. Furthermore, the essential oils that are added in steps 115, 120 and 125 may be added in any order.

In the present embodiment, each ingredient provides novel utility and/or advantages in many practical applications when implemented in light of the teachings of the present invention. The coconut oil acts as the base of the product, stimulates hair follicles and promotes healthy hair growth. Coconut oil helps to keep the hair well moisturized and the hair shaft strong. The oils and proteins in coconut oil work well to help prevent the hair from losing protein, which is one of the major contributors to hair breakage and hair loss. Olive oil has a high level of mono-unsaturated fatty acids and the antioxidant vitamin E that moisturizes, protects, and nourishes hair. Olive oil is very beneficial for dry, damaged, or split hair and can improve its strength and elasticity. Jojoba oil is a liquid wax produced in the seed of the desert plant Simmondsia Chinensis. It is smooth and not greasy and has a close similarity to sebum, natural skin oil. Jojoba oil restores natural moisture to the hair and scalp and helps repair damage; it also helps control scalp sebum. Numerous scalp problems originate from the accumulation of sebum. Jojoba oil acts as a scalp cleanser that can alleviate years of encrusted buildup on the scalp that can cause follicle blockage and impede normal hair growth. Jojoba oil penetrates the scalp, loosening and dissolving the hardened layer of sebum and allowing the other ingredients of the present embodiment to penetrate deep into the scalp. Also, the unique antioxidant properties of jojoba oil help to protect the hair from damage, ultimately keeping the hair healthier. Rosemary essential oil has been found to stimulate hair follicles to produce new hair growth while inhibiting the natural shedding process. Lavender oil has been found to help stimulate the hair growth process and balance normal hair oil production. Human clinical studies have reported that lavender oil has been beneficial in treating alopecia (i.e., hair loss) and has antibacterial and antiviral properties.

Methylsulfonylmethane is a natural organic sulfur compound found in all living things. It helps to make the cell walls more permeable, which increases circulation. Good circulation is a key component in the natural hair growth process. In addition, methylsulfonylmethane repairs and creates healthy cells and has been found to lengthen the natural hair growth phase, or anagen phase, thus allowing hair to grow more rapidly and achieve greater lengths. Biotin is a major component in the natural hair manufacturing process and is an essential nutrient to grow new hair. It potentially promotes hair growth, protects against dryness, and increases the elasticity of the hair, thus generally preventing breakage.

*Eclipta Alba*, an herbal plant, has been found beneficial for many ailments one of which includes hair loss. It is useful for promoting hair growth and generally preventing hair loss and dandruff and promoting healthy long hair. *Emblica Officinalis*, Amalaki, is well known in Ayurvedic medicine. All parts of the plant are used in various Ayurvedic herbal preparations. It has been found to provide nutrients that enrich hair growth and hair pigmentation thus helping to stimulate hair growth and control premature graying of the hair.

Daily applications of the hair oil formulation according to the present embodiment have been found to promote the growth of hair in areas of the scalp that had exhibited no growth. Applications of the formulation every other day have been found to promote the growth of hair in areas exhibiting little or slow growth. Applications of the formulation have been found to promote the growth of hair for the purposes of lengthening when applied one to two times a week. The product is typically used at regular intervals, preferably 3 to 5 times per week, on hair that has been washed a minimum of once a week. The average growth of hair is ¼ inch per month. After being treated with this hair care formulation, users may potentially see an increase in this average hair growth. In addition, users with areas of very thin hair due to conditions such as, but not limited to, male pattern baldness who use a hair growth formulation according to the present embodiment as described above once a day may see the size of these thinning areas decrease or even disappear. Users of a formulation according to the present embodiment may even see new hair growth from areas of the scalp that were once completely bald.

Having fully described at least one embodiment of the present invention, other equivalent or alternative methods of providing a hair treatment for promoting hair health and growth according to the present invention will be apparent to those skilled in the art. The invention has been described above by way of illustration, and the specific embodiments disclosed are not intended to limit the invention to the particular forms disclosed. For example, the particular implementation of the formulation may vary depending upon the particular type of treatment used. The formulation described in the foregoing was directed to topical hair oil implementations; however, similar techniques are to implement the formula in other types of hair treatments such as, but not limited to, shampoos, conditioners, tonics, and styling products including, but not limited to, moose, gel and hairspray. Non-oil implementations of the present invention are contemplated as within the scope of the present invention. The invention is thus to cover all modifications, equivalents, and alternatives falling within the spirit and scope of the following claims.

Claim elements and steps herein have been numbered and/or lettered solely as an aid in readability and understanding. As such, the numbering and lettering in itself is not intended to and should not be taken to indicate the ordering of elements and/or steps in the claims.

What is claimed is:
1. A method for making a topical hair care formulation, said method comprising the following steps:
   a) combining herbal powders to form a herbal powder mixture I;

b) steeping said herbal powder mixture I resulting from step a) to form a brown solution;
c) combining biotin and Methylsulfonylmethane to form a mixture II;
d) combining olive oil with said brown solution resulting from step b) to form a mixture III;
e) combining jojoba oil with said mixture III resulting from step d) to form a mixture IV;
f) combining rosemary essential oil with said mixture IV resulting from step e) to form a mixture V;
g) combining lavender essential oil with said mixture V resulting from step f) to form a mixture VI;
h) combining said mixture II resulting from step c) with said mixture VI resulting from step g) to form a mixture VII; and
i) settling said mixture VII resulting from step h) to form the topical hair care formulation.

2. The method as recited in claim 1, further comprising removing herbal powder residuals resulting from the settling process in step i).

3. A method for making a topical hair care formulation, said method comprising the following steps:
a) combining substantially equal amount of *Eclipta Alba* herbal powder and *Emblica officinalis* herbal powder to form a herbal powder mixture I;
b) steeping said herbal powder mixture I resulting from step a) with base oil for a period of time to form a brown solution;
c) combining a portion of olive oil with an effective amount of biotin and an effective amount of Methylsulfonylmethane to form a mixture II;
d) combining a remainder of olive oil with said brown solution resulting from step b) to form a mixture III;
e) combining an effective amount of jojoba oil with said mixture III resulting from step d) to form a mixture IV;
f) combining an effective amount of rosemary essential oil with said mixture IV resulting from step e) to form a mixture V;
g) combining an effective amount of lavender essential oil with said mixture V resulting from step f) to form a mixture VI;
h) combining said mixture II resulting from step c) with said mixture VI resulting from step g) to form a mixture VII; and
i) settling said mixture VII for a period of time to form the topical hair care formulation.

4. The method as recited in claim 3, further comprising removing herbal powder residuals resulting from the settling process in step i).

5. The method as recited in claim 3, wherein the steeping process in step b) further comprises placing the herbal powder mixture I in a cloth bag.

6. The method as recited in claim 3, wherein said base oil in step b) is coconut oil.

7. The method as recited in claim 3, wherein said base oil in step b) is avocado oil.

8. The method as recited in claim 3, wherein said olive oil in steps c) and d) is extra virgin olive oil.

9. The method as recited in claim 3, wherein said lavender essential oil in step g) is French lavender essential oil.

10. A topical hair care formulation comprising:
a) an effective amount of herbal powders steeped in an effective amount of base oil, wherein said herbal powders comprise an effective amount of *Eclipta Alba* plant and an effective amount of *Emblica Officinalis* plant;
b) an effective amount of biotin and an effective amount of methylsulfonylmethane mixed with an effective amount of olive oil;
c) an effective amount of jojoba oil;
d) an effective amount of rosemary essential oil; and
e) an effective amount of lavender essential oil.

11. The topical hair care formulation as recited in claim 10, wherein said base oil comprises coconut oil.

12. The topical hair care formulation as recited in claim 10, wherein said base oil comprises avocado oil.

13. The topical hair care formulation as recited in claim 10, wherein said olive oil is extra virgin olive oil.

14. The topical hair care formulation as recited in claim 10, wherein said lavender essential oil is French lavender essential oil.

15. The topical hair care formulation as recited in claim 10, wherein the ratio of said effective amount of *Eclipta Alba* to said effective amount of *Emblica Officinalis* is 1 to 1.

16. The topical hair care formulation as recited in claim 10, wherein the ratio of said effective amount of base oil to said effective amount of olive oil is 2 to 1.

17. The topical hair care formulation as recited in claim 10, wherein the ratio of said effective amount of base oil to said effective amount of jojoba oil is 6.7 to 1.

18. The topical hair care formulation as recited in claim 10, wherein the ratio of said effective amount of base oil to said effective amount of lavender essential oil is 209 to 1.

19. The topical hair care formulation as recited in claim 10, wherein the ratio of said effective amount of base oil to said effective amount of rosemary essential oil is 94 to 1.

20. The topical hair care formulation as recited in claim 10, wherein the ratio of said effective amount of methysulfonylmethane to said effective amount of biotin is 200 to 1.

\* \* \* \* \*